United States Patent
Murakami et al.

(10) Patent No.: US 8,836,941 B2
(45) Date of Patent: Sep. 16, 2014

(54) METHOD AND APPARATUS TO PREPARE A SUBSTRATE FOR MOLECULAR DETECTION

(75) Inventors: Makoto Murakami, Ann Arbor, MI (US); Yong Che, Ann Arbor, MI (US); Bing Liu, Ann Arbor, MI (US); Yuki Ichikawa, Ann Arbor, MI (US)

(73) Assignee: IMRA America, Inc., Ann Arbor, MI (US)

( * ) Notice: Subject to any disclaimer, the term of this patent is extended or adjusted under 35 U.S.C. 154(b) by 31 days.

(21) Appl. No.: 12/951,524

(22) Filed: Nov. 22, 2010

(65) Prior Publication Data

US 2011/0194106 A1 Aug. 11, 2011

Related U.S. Application Data

(60) Provisional application No. 61/303,014, filed on Feb. 10, 2010.

(51) Int. Cl.
| | | |
|---|---|---|
| *G01J 3/44* | (2006.01) | |
| *C23C 14/08* | (2006.01) | |
| *B82Y 30/00* | (2011.01) | |
| *C23C 14/34* | (2006.01) | |
| *G01N 21/65* | (2006.01) | |
| *B82Y 40/00* | (2011.01) | |

(52) U.S. Cl.
CPC ............ *G01N 21/658* (2013.01); *C23C 14/083* (2013.01); *B82Y 30/00* (2013.01); *C23C 14/3435* (2013.01); *B82Y 40/00* (2013.01)
USPC ........................................................ 356/301

(58) Field of Classification Search
USPC ........................................................ 356/301
See application file for complete search history.

(56) References Cited

U.S. PATENT DOCUMENTS

| | | | |
|---|---|---|---|
| 5,476,535 A * | 12/1995 | Khasin ............................. | 75/345 |
| 6,242,264 B1 * | 6/2001 | Natan et al. .................... | 436/171 |
| 7,192,778 B2 | 3/2007 | Natan | |
| 7,608,308 B2 | 10/2009 | Liu et al. | |
| 7,864,312 B2 | 1/2011 | Mazur et al. | |
| 7,879,410 B2 | 2/2011 | Che et al. | |
| 8,246,714 B2 | 8/2012 | Liu et al. | |
| 2001/0053521 A1 * | 12/2001 | Kreimer et al. .................... | 435/6 |
| 2006/0252065 A1 | 11/2006 | Zhao et al. | |

(Continued)

FOREIGN PATENT DOCUMENTS

WO WO 2004000491 A3 * 5/2004

OTHER PUBLICATIONS

Oxford Instruments, http://www.oxford-instruments.com/products/etching-deposition-growth/processes-techniques/plasma-deposition/pvd/Pages/pvd.aspx, Jan. 12, 2009.*
Besner at al. Appl. Phys. A 88, 269-272 (2007).*

(Continued)

*Primary Examiner* — Kara E Geisel
*Assistant Examiner* — Hina F Ayub
(74) *Attorney, Agent, or Firm* — Dickinson Wright PLLC

(57) ABSTRACT

An device for Raman spectroscopy such as surface enhanced Raman spectroscopy (SERS) is disclosed herein. Various embodiments may be utilized to prepare a SERS substrate using several deposition techniques such as pulsed laser deposition. Some embodiments optimize coverage, volume, or elements of SERS active metals. The method is a single step inexpensive method for preparing a SERS active substrate. In some embodiments a coating layer underneath the SERS active metals is utilized for additional enhancements.

25 Claims, 13 Drawing Sheets

(56) References Cited

U.S. PATENT DOCUMENTS

| | | | |
|---|---|---|---|
| 2007/0165217 A1* | 7/2007 | Johansson et al. | 356/301 |
| 2008/0187684 A1 | 8/2008 | Hu et al. | |
| 2008/0193667 A1* | 8/2008 | Garbar et al. | 427/532 |
| 2008/0266555 A1* | 10/2008 | Murphy et al. | 356/301 |
| 2008/0286488 A1* | 11/2008 | Li et al. | 427/541 |
| 2009/0033929 A1 | 2/2009 | Mazur et al. | |
| 2009/0246413 A1* | 10/2009 | Murakami et al. | 427/596 |
| 2009/0246530 A1 | 10/2009 | Murakami et al. | |
| 2009/0249520 A1* | 10/2009 | Anderson | 850/30 |
| 2009/0258355 A1* | 10/2009 | Maye et al. | 435/6 |
| 2009/0279085 A1 | 11/2009 | Ebstein | |
| 2009/0311513 A1 | 12/2009 | Hu et al. | |
| 2010/0227133 A1 | 9/2010 | Liu et al. | |

OTHER PUBLICATIONS

International Search Report Dated Apr. 20, 2011—2 Pages.

A. Tao et al., "Langmuir-Blodgettry of Nanocrystals and Nanowires" Accounts of Chemical Research vol. 41 (2008) 1662-1673.

B. Yan et al., "Engineered SERS substrates with multiscale signal enhancement: Nanoparticle cluster arrays" American Chemical Society-AC Nano, vol. 3 (2009) 1190-1202.

Yoshida et al., "Nanometer-sized Silicon Crystallites Prepared by Excimer Laser Ablation in Constant Pressure Inert Gas", Appl. Phys. Lett. 68, pp. 1772-1776, 1996.

* cited by examiner

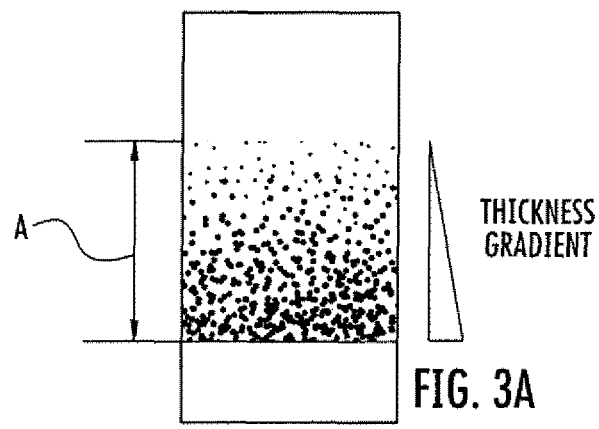
FIG. 3A
|   | 1 | 2 | 3 | 4 |
|---|---|---|---|---|
| A |   | A1 | A2 | A3 | A4 |
| B |   | B1 | B2 | B3 | B4 |
| C |   | C1 | C2 | C3 | C4 |
| D |   | D1 | D2 | D3 | D4 |
FIG. 3B
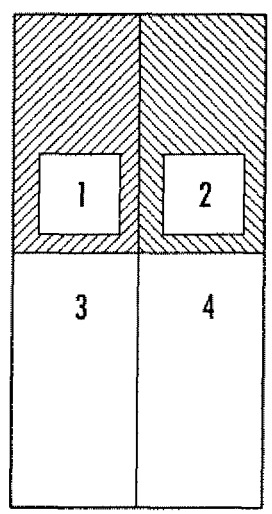
FIG. 3C

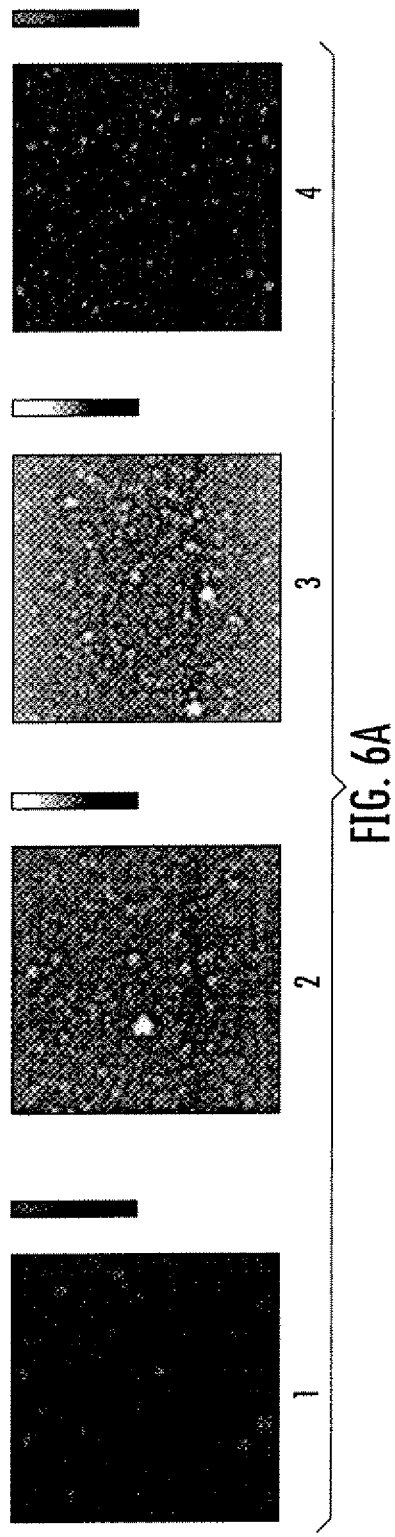
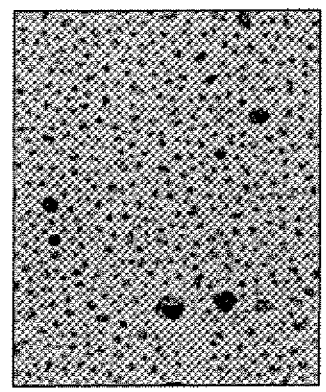
FIG. 6A
FIG. 6B

US 8,836,941 B2

METHOD AND APPARATUS TO PREPARE A SUBSTRATE FOR MOLECULAR DETECTION

RELATED APPLICATIONS

This application claims the benefit of U.S. provisional application Ser. No. 61/303,014 filed Feb. 10, 2010.

The subject matter of this application is related to U.S. patent application Ser. No. 11/405,020 filed on Apr. 17, 2006 and issued on Oct. 27, 2009 as U.S. Pat. No. 7,608,308, entitled "P-type Semiconductor Zinc Oxide Films Process for Preparation Thereof, and Pulsed Laser Deposition Method Using Transparent Substrates". The subject matter of this application is also related to U.S. patent application Ser. No. 12/401,967 entitled "A Method for Fabricating Thin Films", filed on Mar. 11, 2009, which claims priority to U.S. patent application Ser. No. 12/254,076 entitled "A Method for Fabricating Thin Films", filed on Oct. 20, 2008, and which claims priority to U.S. Provisional Application No. 61/039,883, entitled "A Method for Fabricating Thin Films", filed Mar. 27, 2008. The subject matter of this application is also related to U.S. patent application Ser. No. 11/798,114 filed May 10, 2007 and entitled "Method for Depositing Crystalline Titania Nanoparticles and Films", which claims priority to U.S. Provisional Application No. 60/899,892 filed on Feb. 7, 2007. This application is also related to U.S. patent application Ser. No. 12/400,438 filed on Mar. 9, 2009 and entitled "Ultrafast Pulsed Laser Micro-Deposition Pattern Formation".

The disclosures of application Ser. Nos. 11/405,020, 61/039,883, 11/798,114, 60/899,892, 12/254,076, 12/400,438, and 12/401,967 are hereby incorporated by reference in their entirety.

STATEMENT REGARDING FEDERALLY SPONSORED RESEARCH

NONE

TECHNICAL FIELD

This invention relates to a method for preparing a substrate surface or support material having a surface for detection of materials and compounds such as organic molecules and biomolecules by Raman scattering.

BACKGROUND

Surface enhanced Raman scattering or surface enhanced Raman spectroscopy (SERS) is a very sensitive and valuable analytical tool that enhances Raman scattering by molecules adsorbed onto or located on certain SERS active metal surfaces. The signal enhancement can be as high as $10^{14}$ or $10^{15}$, thus the method can be used to detect single molecules of interest. The exact mechanism of the enhancement is not currently known, although there are two prevailing theories. One theory, the electromagnetic theory, is that the enhancement results from excitation of localized surface plasmons. The chemical theory, on the other hand, attributes the enhancement to formation of charge-transfer complexes. The chemical theory, however, only applies to species that have formed a bond with the surface so it can not explain the enhancement in all cases whereas the electromagnetic theory is broader in application. Typical surfaces for SERS comprise particles or roughened surfaces of silver, gold, copper, palladium, or platinum. To get the SERS effect the surfaces must be rough, they can not be smooth. The surface can be prepared either by roughening a smooth surface of the metal or by depositing nanometer sized metal particles onto a surface. The shape and size of the nanoparticles and the thickness of the nanoparticle layer all effect the SERS signal. Because SERS requires a rough metal surface, conventional thin film growth techniques, which produce smooth thin films, are not suitable for forming SERS substrates.

One method for making a SERS substrate is to drop-cast or spread, a solvent, which contains nanoparticles, onto a surface; however, this method suffers from non-uniformity of the SERS active area, a lack of reproducibility, and inconsistent signal enhancement. Yet another method for formation of SERS surfaces is the chemical assembly method, which is also called the Langmuir-Blodgett (LB) method as disclosed in A. Tao et al., "Langmuir-Blodgettry of Nanocrystals and Nanowires" Ace. Chem. Res. Vol. 41. (2008) 1662-1673. In the LB method, noble metal nanoparticles are modified with hydrophobic molecules then dispersed in a volatile compound that is immiscible in water. This method is relatively simple and may be used on large-scale applications; however, the stability of the nanoparticle solution can be an issue.

In another method a substrate which provides a support material or a base is prepared by coating a patterned surface with a metal. First a pattern is imprinted into the surface. Then, SERS active metals are electrochemically or physically coated onto the patterned surface, to enhance the SERS signal as disclosed in B. Yan et al., "Engineered SERS substrates with multiscale signal enhancement: Nanoparticle cluster arrays" ACS Nano, Vol. 3. (2009) 1190-1202. This method requires several steps to obtain the desired SERS substrate and is typically expensive due to the required equipment used to produce the surfaces such as photo- or electron- lithography.

In yet another method a support material surface is first modified by laser nanomachining and then coated with a SERS active metal. For example, femtosecond laser processing has been used to prepare nanostructure surfaces which are then coated with reactive metals for SERS and other photonic sensing methods; however, the method still requires multiple steps to prepare the substrate as disclosed in U.S. Pat. No. 7,586,601. This method claims to be inexpensive compared with other patterned substrates based on lithography techniques discussed above, but it is still a multistep process and time consuming.

It is highly desirable to develop a method for producing a SERS active metal surface on a substrate that is inexpensive, rapid to carry out, highly reproducible, and tunable for detection of various substances.

SUMMARY OF THE INVENTION

The present invention comprises a method of forming a SERS active metal surface on a substrate for Raman spectroscopy and the product formed by the method. The method comprises the steps of providing a substrate or support material having a relatively flat surface and applying a nanostructured metal layer to the surface in a single step by a process comprising ultrashort pulsed laser deposition, ultrashort backside transfer pulsed laser deposition, or sputtering, thereby forming the substrate for Raman spectroscopy. The product can be used in surface enhanced Raman spectroscopy (SERS), surface enhanced resonance Raman spectroscopy (SERRS), surface enhanced hyper Raman spectroscopy (SEHRS), surface enhanced coherent anti-Stokes Raman spectroscopy (SECARS), and surface enhanced infrared absorption (SEIRA). The method is rapid, inexpensive, highly reproducible and tunable for optimization of detection based on the active metal used or the substance being detected. The method permits a thickness gradient of the active metal layer to be applied to the surface so that the optimum thickness for detection of a compound of interest can easily be determined by coordinating signal intensity with position on the gradient. The method also permits the substrate surface to be pre-coated with other materials prior to applying the active metal surface to enhance the Raman signal derived from the active metal layer. In this embodiment, the SERS active metal is not directly bonded to the substrate surface.

BRIEF DESCRIPTION OF THE DRAWINGS

FIGS. 3A-3C illustrate a sample description of a thickness gradient thin film, a different roughness library, and a coating library, respectively, according to the present invention;

FIG. 6A shows Atomic Force Microscope images of Au thickness gradient thin films on a sapphire substrate and FIG. 6B shows a transmission electron microscope (TEM) image of Au nanoparticles prepared according to the present invention;

DETAILED DESCRIPTION

As noted above, it is highly desirable to develop a method for producing a SERS active metal surface on a substrate that is inexpensive, rapid to carry out, highly reproducible, and tunable for detection of various substances including organic and biological molecules. The present invention is a simplified one step process for preparing SERS actaive metal surfaces on substrates having improved reliability, improved reproducibility, reduced cost, and being tunable for optimization of the detection of specific molecules. The present invention utilizes pulsed laser deposition (PLD), particularly using ultrafast lasers, to fabricate a functional SERS active metal surface on a surface of a support material in a single step process. When compared to the commercially available SERS substrate, Klarite®, a SERS substrate prepared according to the present invention shows a better sample detection signal with less fluorescent background signal from the substrate. As noted above, the SERS active metal surface does not have to be applied directly to the substrate surface, there can be one or more intervening layers as shown below. In the present specification and claims coating a surface of a substrate with an active metal coating does not require direct application to the surface, i.e. there can be intervening layers, unless so specified.

Figure 1A:
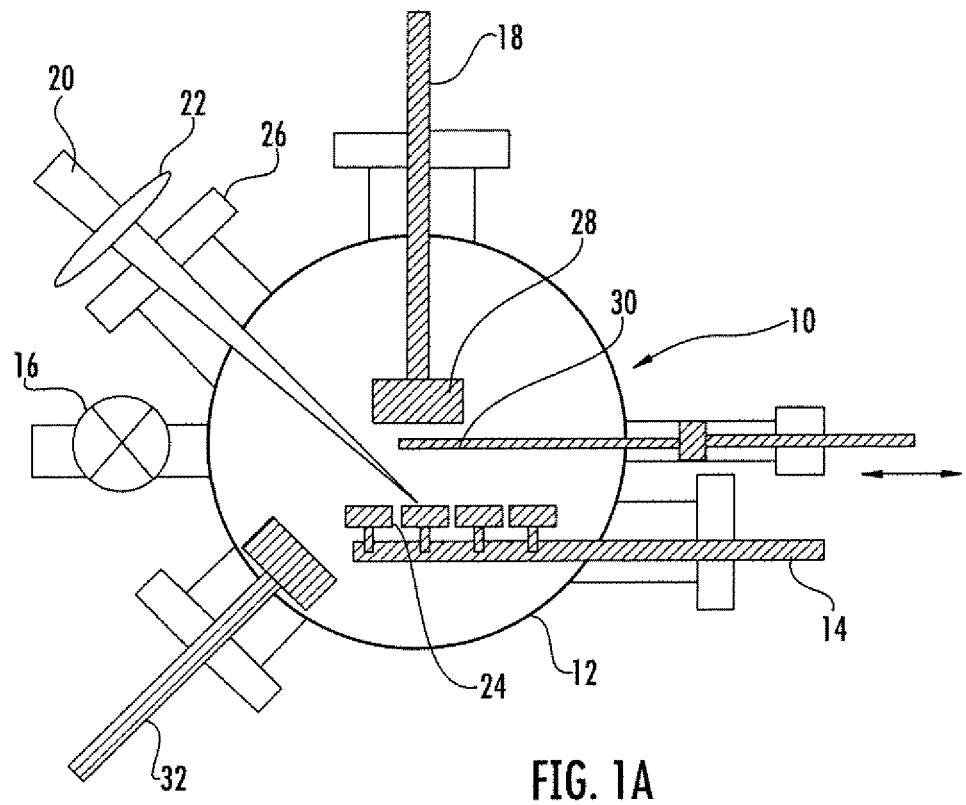
FIG. 1A schematically illustrates several components of a pulsed laser deposition system according to the present invention and FIG. 1B schematically illustrates several key components for the present invention.
Figure 1B:
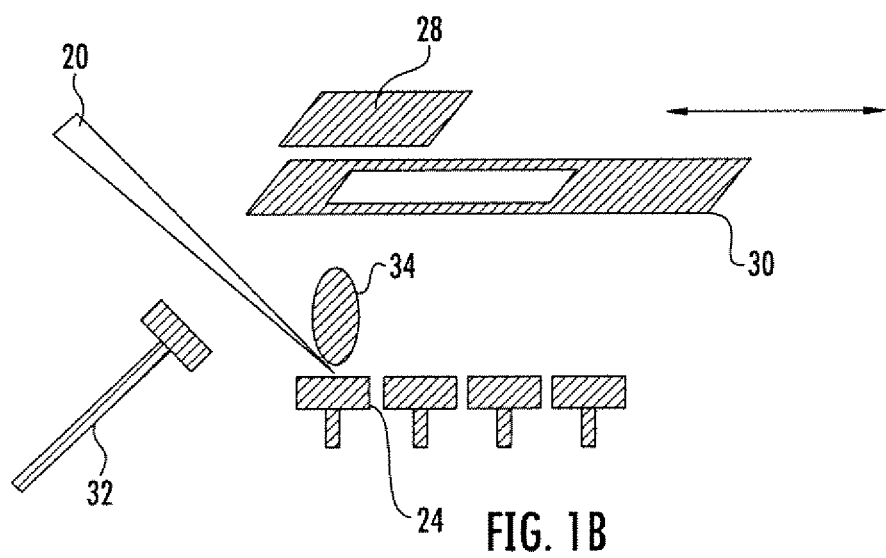

In accordance with one embodiment, FIGS. 1A and 1B schematically illustrate several elements of a pulsed laser deposition (PLD) system and an experimental arrangement used to carry out the experiments disclosed herein. The PLD system used in various embodiments of the present invention is similar to that described in U.S. patent application Ser. No. 12/401,967, filed Mar. 11, 2009 and entitled "A Method for Fabricating Thin Films", which illustrates operation of burst-mode pulses. A PLD system 10 includes a vacuum chamber 12 and related turbo and mechanical pumps, not shown in the figure, a target manipulator 14, a gas inlet 16, and a substrate manipulator 18. A laser beam 20 is focused by a lens 22 onto a target 24 surface through a fused silica window 26. The target manipulator 14 provides rotational and lateral movements to a plurality of target 24 materials, while the substrate manipulator 18 provides heating and rotational and lateral movements to a substrate 28 or support material. The gas inlet 16 provides gases to the vacuum chamber 12 and is used to adjust their pressures. The vacuum chamber 12 and associated pumps are capable of producing conditions from atmospheric pressure down to very high vacuums of $1 \times 10^{-10}$ mbar. Additional features of the PLD system 10 according to the present invention comprise a movable shadowing mask 30 and a magneto sputtering gun 32. The shadowing mask 30, which is equipped with a linear motion feedthrough, is used to cover or uncover the substrate 28 completely or partially during the PLD process. The present inventive single step method only requires the growth of SERS active metal thin films onto a substrate 28 surface. The mask 30 can be used to prevent a plasma plume 34 generated during the PLD process from being deposited onto a portion of the substrate 28. By moving the mask 30 during the PLD process, a graduated series of thicknesses of SERS active material can be deposited on a substrate 28. In some embodiments the laser beam 20 may be scanned using Galvanometer based scanning system, not shown, across a target 24. The direction of the laser beam 20 scanning may be perpendicular or lateral to the target 24. The magneto sputtering gun 32 can be used to deposit materials onto the substrate 28 either before or after the SERS active metal coating is deposited. The substrates or support materials useful in various embodiments of the present invention comprise a wide variety of surfaces including glass, silicon, $Al_2O_3$, organic films, and metal foils.

In the process of the present invention the PLD system laser is preferably operated in a "burst mode" to grow the SERS active metal coatings on a surface of the substrate. Each burst includes a train of laser beam pulses closely separated in time. Pulse parameters, such as the number of pulses in the burst, the burst repetition rate, and the laser beam fluence may be varied to provide tunable size control in growth of nanoparticles on the substrate. In the method, the burst may be generated via a number of processes known to those of skill in the art. In one process the bursts are generated by optical beam splitting and recombining using a beam splitter and a delay stage. In another process, the burst is achieved via an acousto-optic modulator (AOM) that is used for pulse selection in a chirped pulse amplification (CPA) system, and the burst width and burst repetition rate are determined by the gate width and repetition rate of the AOM, respectively.

Figure 2A:
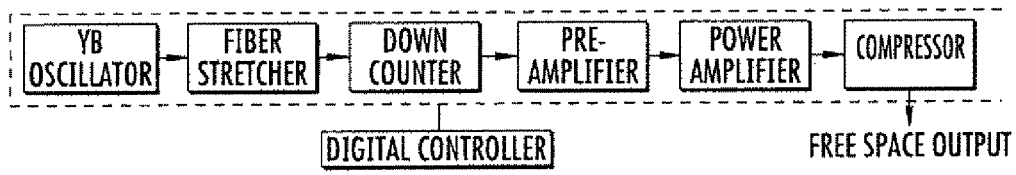
FIGS. 2A-2C schematically illustrate a pulsed laser system and some examples of laser parameters useful for tuning thin film properties in accordance with the present invention.

FIG. 2A illustrates a fiber-based chirped pulse amplification system for producing ultrashort pulses in accordance with the present invention. A commercially available laser capable of producing sub-picosecond pulses is the model FCPA µJewel D-1000 from IMRA America, Inc. A down counter or pulse picker is used to reduce the repetition rate of the oscillator from about 1 MHz to 1 GHz down to a repetition rate in the range of 100 kHz to about 5 MHz. For example, if the oscillator rate is 50 MHz and pulses are selected at a rate of 1:50, the resulting output repetition rate is 1 MHz. The standard D-1000 configuration provides for a repetition rate between 100 kHz and 5 MHz, with a corresponding variation in pulse energy and pulse width. For example, a pulse energy of about 10 microJoules is specified for 100 kHz operation. For 5 MHz operation a pulse energy of a few hundred nanoJoules is available. Sub-picosecond pulses can be generated, for example pulse widths in a range of about 700 femtoseconds to about 1 picoseconds. The "burst mode" PLD system may include a user interface providing access to the digital controller of FIG. 2A. The down counter or other suitable pulse picker is programmed so that the number of pulses, pulse spacing, pulse intensity, and burst intensity profile meaning the envelope defined by the pulses of the burst are adjustable over a reasonable range, for example about 10:1.

Figure 2B:
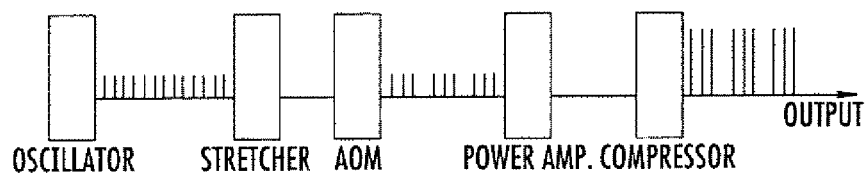

FIG. 2B schematically illustrates how the output pulses are generated. In this example a mode locked oscillator operates at a high repetition rate for example, at 50 MHz or greater. Pulses from the mode locked source are temporally stretched prior to amplification with the power amplifier. Selection of one or more pulses is carried out by the Acousto-Optic Modulator (AOM) or another suitable pulse picker to generate output pulses and to control the effective output pulse repetition rate. The number of pulses in each burst is determined by the AOM gate width, meaning the time duration during which the switch is open. For example, a typical oscillator generates pulses with a high repetition rate of 50 MHz, therefore with a pulse interval of 20 nanoseconds. Thus, if the AOM gate opens each time for 100 nanoseconds, the output burst mode will have 5 pulses in each burst, and the burst repetition rate will be determined by the AOM repetition rate.

Figure 2C:
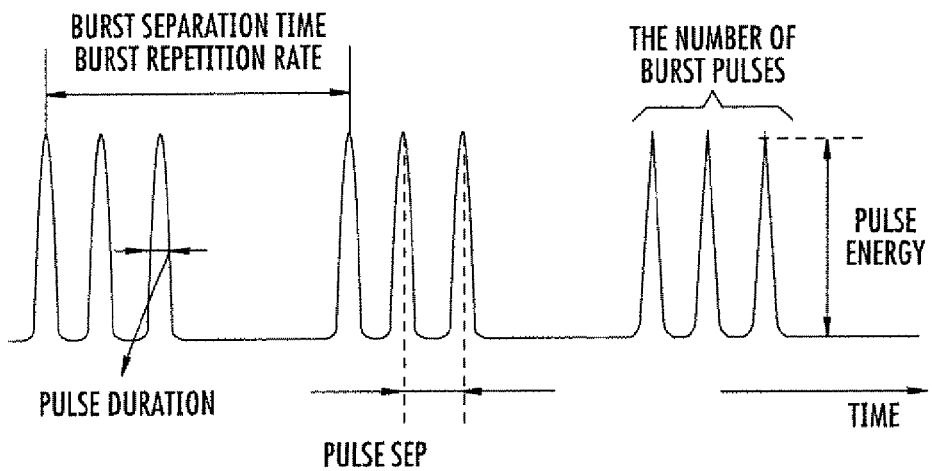

FIG. 2C schematically illustrates a laser pulse train in burst mode and some of the laser parameters used to tune the surface morphology of the thin films of SERS active metal deposited according to the present invention. Each burst includes a group of closely spaced pulses. The adjustable laser parameters include pulse duration, burst repetition rate, pulse separation time, number of pulses per burst, and pulse energy. Tuning the thin film roughness can be achieved by varying these laser parameters. For a typical pulse amplification system, the base repetition rate, meaning the repetition rate of the pulses within the bursts, is determined by the oscillator repetition rate, which is possible to change.

In some of the embodiments of the present invention when using PLD the number of pulses per burst can be varied from 1 to 100, more preferably the number of pulses per burst is from 2 to 50. The burst repetition rate is preferably from 1 kHz to 100 MHz. The pulse repetition rate preferably is from 1 MHz to 1 GHz with a pulse separation of from 1 nanosecond to 1 microsecond, or a repetition rate of 100 kHz to 100 MHz. The pulse energy can range from 1 nanoJoules to 10 milliJoules, more preferably from 10 nanoJoules to 100 microJoules, most preferably from 50 nanoJoules to 10 microJoules. The laser fluence is preferably from 1 milliJoules/cm$^2$ to 100 Joules/cm$^2$ and more preferably from 10 milliJoules/cm$^2$ to 50 Joules/cm$^2$. The pulse width can be from 10 femtoseconds to 100 nanoseconds, more preferably from 1 picoseconds to 200 picoseconds. The laser beam wavelength can be from 200 nanometers to 2000 nanometers depending on the source. The laser beam focused spot diameter can be from 5 microns to 500 microns, more preferably from 10 to 450 microns. Using such a system, in general, as the number of pulses per burst and the burst repetition rate increases the particle size decreases. Use of ultrashort lasers per the present invention provides three main benefits. The short pulse duration of femtoseconds to picoseconds means that there is a high peak power density. Therefore, the ablation threshold is reduced by 1 to 2 magnitudes so the total pulse energy can be reduced to the microJoule range rather than the milliJoule range. In addition, there is a much reduced heat zone so there is less splatter of drops during deposition.

FIG. 3A is a schematic illustrating a thickness gradient of a thin film of a SERS active metal applied to a substrate according to the present invention. The amount of SERS active metal, for example Au or Ag, deposited is continuously and linearly varied in region A to produce a coating wherein the thickness of the SERS active metal coating varies. The thickness at a given position is determined using a microbalance monitor from Inficon. This gradient layer is accomplished using movement of the mask as the target material is being deposited onto the substrate. By observing the position dependence of the surface morphology and Raman spectroscopy results, variations in the SERS active metal thickness can be used to optimize SERS measurements.

FIG. 3*b* illustrates a schematic of a substrate table for studying the effect of roughness and/or materials dependence with different thicknesses of metals deposited according to the present invention. Preceding the SERS active metals coating, three different roughness of $TiO_2$ thin films are coated onto a glass substrate surface. The $TiO_2$ thin films are prepared using burst-mode fs-PLD, which was previously disclosed by the inventors of this application. When using a higher number of burst pulses the resulting thin film surface is smoother. First, smooth $TiO_2$ thin films, using 23 burst pulses, were coated onto columns 1, 2, and 3, while column 4 is kept as bare glass. Second, the next roughest $TiO_2$ thin films, using 5 burst pulses, were coated onto columns 1 and 2 over the existing $TiO_2$ film. Finally, the roughest $TiO_2$ thin film, using a single pulse, was coated onto column 1 over the previous two coats. Since the surface morphology is the most affected by the roughest region, the roughest thin films are created on the surface in columns 1 and 2. The different regions are divided by a shadowing mask as shown in FIG. 1A during the PLD process. Subsequently, different thicknesses of Au thin films are grown in rows onto the substrate columns perpendicular to the $TiO_2$ columns. Thus, this is an example where the SERS active metal is not directly deposited onto the substrate surface. The thicknesses of the Au thin films are for example 1, 5, 20, and 100 nanometers corresponding to rows A-D respectively. The laser power and the burst frequency are set at 5.3 W and 1 MHz, and 2 pulses, respectively to grow the Au films. This gives a grid work of columns 1-4 and rows A-D to study the effect of pre-coating and SERS active metal coating thicknesses.

FIG. 3C is a schematic illustration of another substrate quadrant for studying the effect of the material coating beneath the SERS active metals coating on the SERS enhancement. Again the SERS active metal is not directly applied to the substrate. The substrate is glass and the mask is used to create the quadrants during the process. Quadrants 1 and 2 are first coated with 100 nanometer thick Pt thin films using a DC magneto sputtering coater as known in the art. The substrate is exposed to air once, and then is placed into a vacuum chamber for growth of Au thin films for SERS using the PLD system of the present invention. The Au thin films are grown on quadrants 2 and 4. Quadrant 3 is not coated in either process and remains as bare glass. The Pt thin film could also have been deposited using the PLD according to the present invention.

Figure 4:
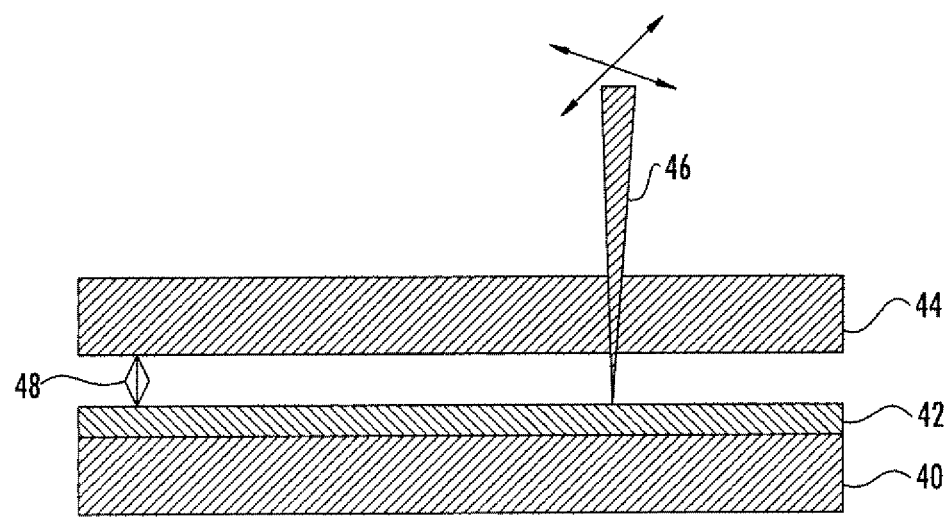
FIG. 4 schematically illustrates a configuration of a backside transfer pulsed laser deposition system in accordance with the present invention.

FIG. 4 schematically illustrates a configuration for backside transfer pulsed laser deposition which can also be used in the present invention to create a substrate coated with a SERS active metal. A target 40 such as glass is pre-coated with a thin film 42 of a SERS active metal such as Au or Ag by a magneto sputtering coater. The thickness of pre-coating film 42 determines the maximum thickness that can be applied to the SERS substrate 44. The target 40 with the film 42 is placed on a plate, not shown, and then a bare substrate 44 such as glass that is transparent to the laser beam wavelength is placed on top of this. A laser beam 46 is irradiated through the transparent substrate 44. The Au thin film is transferred from the target 40 onto the substrate 44. A gap 48 between the film 42 and the substrate 44 can be varied from 0 to 1000 microns, more preferably from 0 to 100 microns. The process of backside transfer PLD is further explained in U.S. Pat. No. 7,608,308 and U.S. application Ser. No. 12/400,438 filed on Mar. 9, 2009. In one example the laser power, burst frequency, and the number of pulses per burst were set at 5W, 200 kHz, and 1 pulse, respectively.

Figure 5:
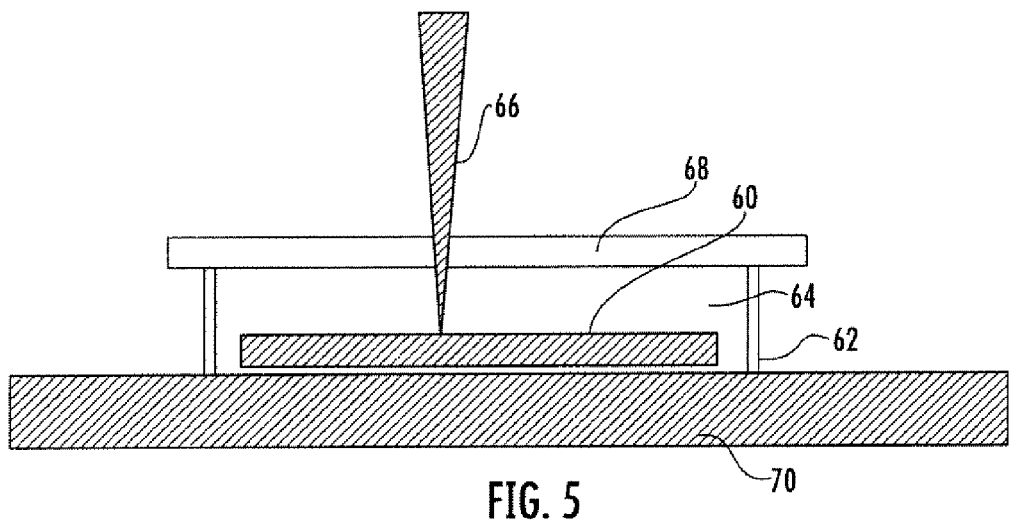
FIG. 5 schematically illustrates a system for Raman measurements in accordance with the present invention.

FIG. 5 illustrates a schematic for making Raman scattering measurements. A substrate 60 with a SERS active metal surface applied according to the present invention is placed face up in a container 62 filled with a solution 64 containing an analyte. The analyte is used to evaluate the SERS enhancement. A laser beam 66 is focused onto the SERS active metal surface of the substrate 60. To prevent evaporation of the solution 64 a glass cover 68 is placed on top of the container 62. A movable XYZ stage 70 is used to adjust the position and focus of the beam 66 relative to the substrate 60. For SERS substrates 60 coated with Au the excitation laser wavelength was 633 nanometers, the slit width was 50 micrometers, the slit density was 1800 lines/millimeter, and the laser spot size was 10 micrometers. For SERS substrates 60 coated with Ag the excitation laser wavelength was 514 nanometers, the slit width was 50 micrometers, the slit density was 1800 lines/millimeter, and the laser spot size was 5 micrometers.

FIG. 6A shows Atomic Force Microscope (AFM) images of SERS active metal Au films on a sapphire substrate. In these images a gradient of Au as described in FIG. 3A was created according to the present invention. The region A was 7 millimeters long and the thickness of the Au film was from 0 to 7 nanometers over that distance. The laser power, burst frequency, and number of pulses per burst used to grow the Au thin films was 6.5 W, 1 MHz, and 2 pulses, respectively. The deposition rate of the Au on the substrate was about 0.03 nanometers/second. As described above the mask was used to create the varied thickness. The thicknesses in images 1-4 of FIG. 6A are 1, 3, 5, and 7 nanometers, respectively. FIG. 6B is a transmission electron microscope (TEM) image of Au nanoparticles fabricated on a carbon coated TEM grid. The thickness is 3 nanometers. From the results it can be seen that there are at least two populations of nanoparticles, one has a particle size of from 2 to 10 nanometers in diameter and another has a particle size of about 25 to 50 nanometers in diameter. The ratio between these two populations can be adjusted by changing the designed thickness or growth conditions of the Au film.

Figure 7A:
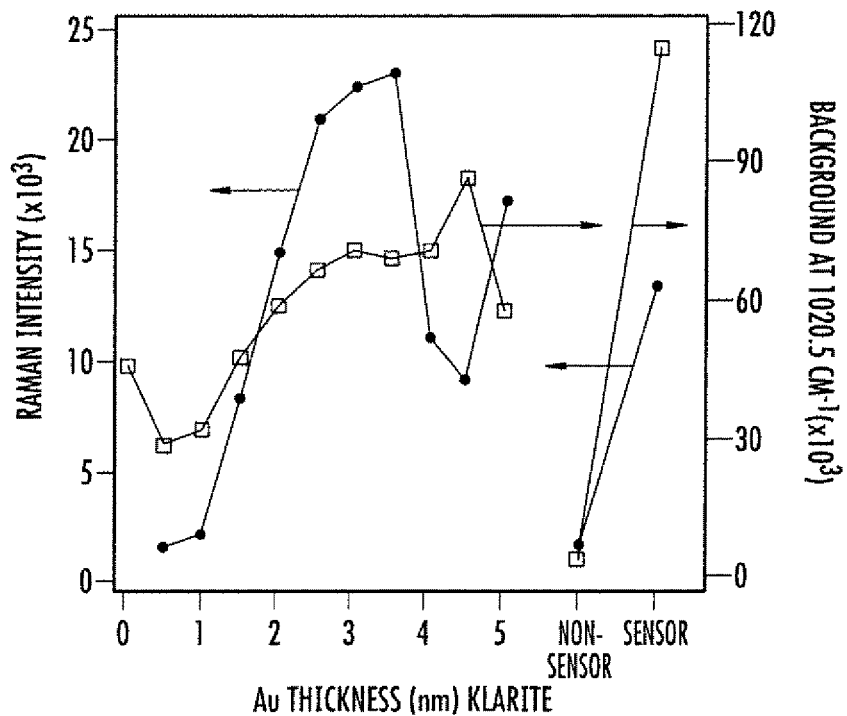
FIGS. 7A and 7B compare the background fluorescence and the Raman spectroscopy signal obtained using a commercially available SERS substrate to substrates prepared according to the present invention.

In FIG. 7A the Raman intensity signal and the fluorescence background signal obtained from a 0.2 weight % pyridine solution in water using either a SERS active metal substrate prepared according to the present invention or a commercial SERS substrate, Klarite™, are compared. The sample prepared according to the present invention comprised a substrate having a gradient of Au as the SERS active metal. The substrate was prepared as described for FIG. 3A and the region A was 7 millimeters long with a thickness gradient of from 0 to 7 nanometers of thickness. The laser power, burst frequency, and number of pulses per burst used to grow the Au thin film according to the present invention were 5.3 W, 1 MHz, and 2 pulses per burst, respectively. The deposition rate was about 0.03 nanometers/second. The commercially available SERS substrate Klarite™ was used as a standard to compare to the substrates of the present invention. The Klarite™ devices were fabricated on silicon wafers coated with gold. The 4 millimeter by 4 millimeter patterned area is shown as Klarite™ sensor in the figures and the non-patterned area is shown as Klarite™ non-sensor. The integration times of these measurements were 100 seconds for the Klarite™ and 200 seconds for the substrate according to the present invention. The data in FIG. 7A shows that around a film thickness of 3 nanometers the Raman intensity peaks and the fluorescent background signal is also reasonably low at this thickness. A SERS enhancement is observed in the sensor area of Klarite™ compared to the non-sensor area, but the signal is not very strong and not nearly as strong as the signal obtained in substrates according to the present invention at a level of 3 nanometers of coating. Also the fluorescent background signal of Klarite™ is very large despite a shorter integration time. It is worth mentioning that the fluorescent background signal increases with increasing integration time, but the peak count does not change with the amount of integration time. It is also noted that the non-sensor area of Klarite™ has a low fluorescent background but does not have high enough SERS signal enhancements.

Figure 7B:
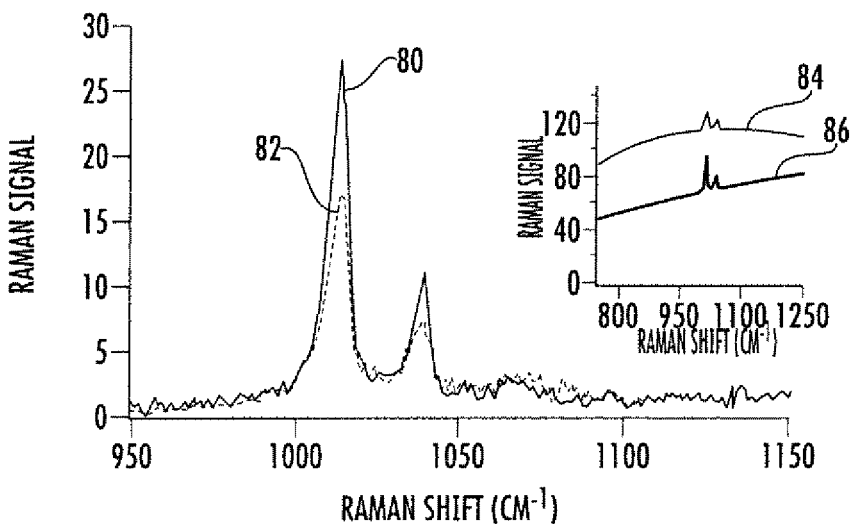
Figure 8A:
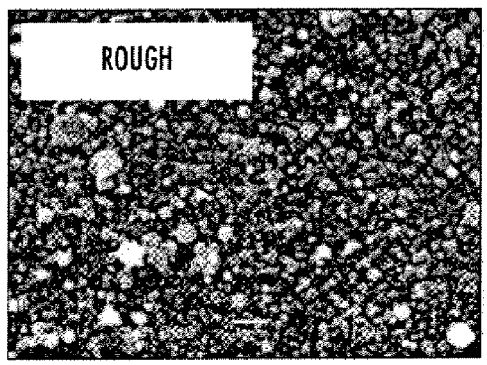
FIG. 8 shows Scanning Electron Micrograph images of a 20 nanometer thick SERS active metal Au coating on bare glass and three different roughness libraries of $TiO_2$ pre-coated thin films.
Figure 8B:
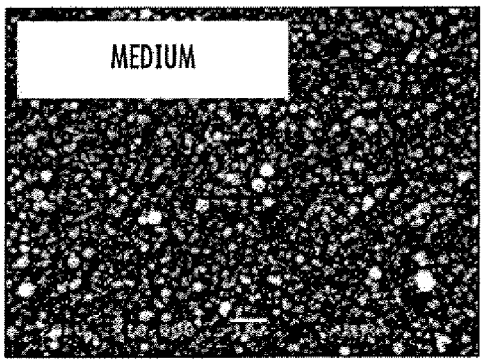
Figure 8C:
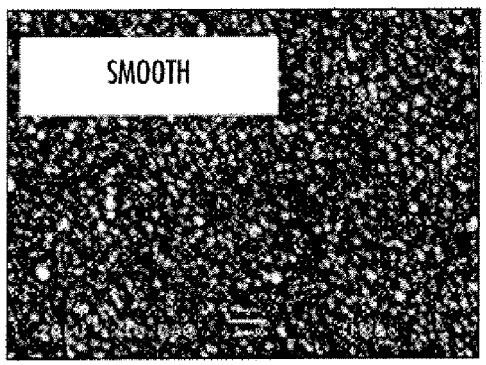
Figure 8D:
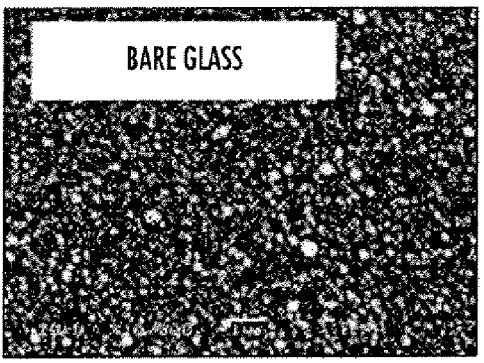

FIG. 7B compares a 3 nanometer thick Au film prepared according to the present invention with the commercial substrate, Klarite™ in detection of a 0.2 weight % pyridine solution. Lines 80 and 86 are the Au films according to the present invention and lines 82 and 84 are the Klarite™ results. The spectra backgrounds were subtracted for comparison in lines 80 and 82. The figure clearly demonstrates that a SERS substrate prepared according to the present invention shows a much higher signal enhancement compared to Klarite™. The inset of the figure illustrates the raw Raman signal, containing the fluorescent background, for both substrates. The Klarite™ has a much higher background and much less SERS signal enhancement. The integration times of these measurements were 100 seconds for the Klarite™ and 200 seconds for the Au film prepared according to the present invention. Another notable result in the present invention is that an Au colloid without surfactant in the water solution could successfully detect the other four Raman-inactive vibration modes of the pyridine molecule which, in general only infrared absorption spectroscopy can observe the peaks such as at about 1400 $cm^{-1}$. Since the present inventive substrate also does not contain any surfactants on the gold surface, the feature would also be detected by the present invention and also be beneficial for a characterization of a specimen.

These results demonstrate the usefulness and value of the present invention and are very promising for making a commercial substrate for SERS detection because the disclosed invention only requires a single step of Au coating onto a substrate. The present process is relatively fast, inexpensive and very reproducible. Additionally, the disclosed invention can easily optimize the Au or other SERS active metal coverage by adjusting the amount of the SERS active metal using the mask. Therefore, depending on the component that is being detected and the selected active metal one can first run a gradient of film thicknesses, choose the one providing the best signal and then create another substrate coated with the SERS active metal at that level. Unlike other disclosed methods, the required amount of SERS active metal is much less. For example, as noted above a thickness of 3 nanometers of Au worked very well for pyridine detection. The other prior art disclosed methods all require thicknesses of from 100 nanometers to 500 nanometers of the SERS active metal coating to provide adequate signals. Thus, the present method provides a tremendous materials cost savings.

Pulsed laser deposition using an ultrashort pulsed laser with a pulse duration less than 200 picoseconds is preferable in the present method, however, if similar nanoparticle aggregate structures can be obtained by using a physical vapor deposition technique such as PLD using a nanosecond pulsed laser or a sputtering process at a high pressure of greater than 100 mbar while controlling the size and dispersion of the nanoparticles, then similar SERS enhancement is expected to be achieved. For example, nanometer sized silicon crystals have been prepared by pulsed laser deposition in high pressure inert gas. See Yoshida et al., Nanometer-sized Silicon Crystallites Prepared By Excimer Laser Ablation In Constant Pressure Inert Gas, Appl. Phys. Lett. 68, pp 1772-1774, 1996.

In addition, since in the present invention the substrate does not have to be heated to grow the SERS active metal thin films, heat sensitive materials such as organic films and metal foils can be used as the substrates coated with the SERS active metals. Examples of these substrates include polymer films such as polyethylene terephalate (PET), polyvinyl chloride (PVC), and one sided or two sided pressure sensitive tapes such as Scotch® tapes; metal sheets such as stainless steel, Cu, and Al; semiconductors such as Si; metal oxide such as glass, $Al_2O_3$, $SrTiO_3$, ZnO, $TiO_2$, and $BaTiO_3$. Preferably the nanostructure produced according to the present invention comprises nanoparticles, nanoparticle aggregates, nanowires, nanorods, nanotubes, nanosheets or mixtures thereof. When the structure comprises nanoparticles preferably they have a size of from 1 nanometer to 1000 nanometers, more preferably from 2 nanometers to 100 nanometers.

The SERS active metal thin films disposed on a substrate according to the present invention need not be in direct contact with the substrate surface as noted above. A thin film layer of another material may be disposed between the substrate surface and the SERS active metal thin film. For example in a next experiment a substrate of glass was precoated with a thin film of $TiO_2$ using burst mode PLD and the PLD parameters were varied to produce different roughness in the $TiO_2$ coatings. The substrates were then coated with a 20 nanometer thick layer of the SERS active metal Au according to the present invention or a 100 nanometer thick layer. When using a higher number of burst pulses the resulting thin film surface is smoother. So to pre-coat the glass substrates first, smooth $TiO_2$ thin films, using 23 pulses per burst, were coated onto regions A, B and C using a laser power of 5W and 1 MHz. Second, regions A and B were again coated with $TiO_2$ thin films, using 5 pulses per burst. This produced a rougher coating on A and B relative to C. Finally, the roughest $TiO_2$ thin film was created on region A by coating using a single pulse per burst. Region D was kept as bare glass substrate and only the Au was coated onto it. Then all the regions were coated with a 20 or a 100 nanometer thick film of the SERS active metal Au according to the present invention. The laser power, burst frequency, and pulses per burst were set at 5.3 W, 1 MHz, and 2 pulses per burst, respectively, for growing the Au films. The Au films were grown perpendicularly to the $TiO_2$ films. FIG. 8 shows Scanning Electron Micrograph (SEM) images of the four regions A-D with 20 nanometer thick Au films. The present inventors confirmed that the 100 nanometer thick Au films also had similar surface morphologies, not shown.

Figure 9:
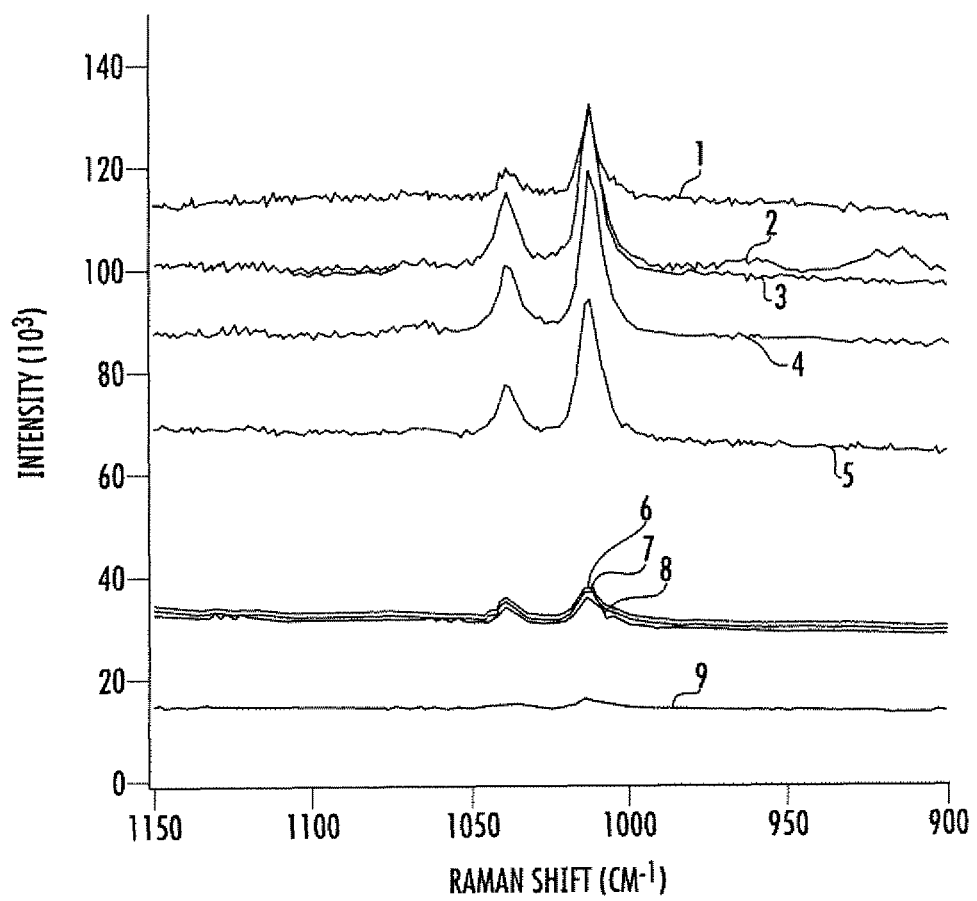
FIG. 9 shows Raman signals of a 0.2 weight % pyridine solution in water using 20 nm or 100 nanometer Au thin films on different roughness $TiO_2$ pre-coated thin films according to the present invention as compared to a commercial product Klarite™.

In FIG. 9 the Raman signal from a 0.2 weight % solution of pyridine in water is shown as detected using the various SERS substrates from FIG. 8. The spectra correspond to the following substrates: line 1 is the commercial product Klarite™; line 2 is 100 nanometers of Au on region B, medium roughness $TiO_2$; line 3 is 100 nanometers of Au on region C, smooth $TiO_2$; line 4 is 100 nanometers of Au on region D, bare glass; line 5 is 100 nanometers of Au on region A, rough $TiO_2$; line 6 is 20 nanometers of Au on region D, bare glass; line 7 is 20 nanometers of Au on region B, medium roughness $TiO_2$; line 8 is 20 nanometers of Au on region C, smooth $TiO_2$; and line 9 is 20 nanometers of Au on region A, rough $TiO_2$.

The data clearly show that the 100 nanometer surfaces produced a much better enhancement than the 20 nanometer surfaces. This probably means that the cross section of the Au is not in large enough amounts on 20 nanometer thick films for the best enhancement. On the other hand, although 100 nanometer thick Au films show higher SERS enhancement, they also have a higher fluorescent background signal. Based on prior knowledge of SERS substrates it was expected that a rougher surface of SERS active metal should show a higher SERS signal. An obvious roughness effect couldn't be found in the data for SERS enhancement, but it is believed that a rougher surface may help reduce the fluorescent background signal as shown by the results in the figure.

Figure 10A:
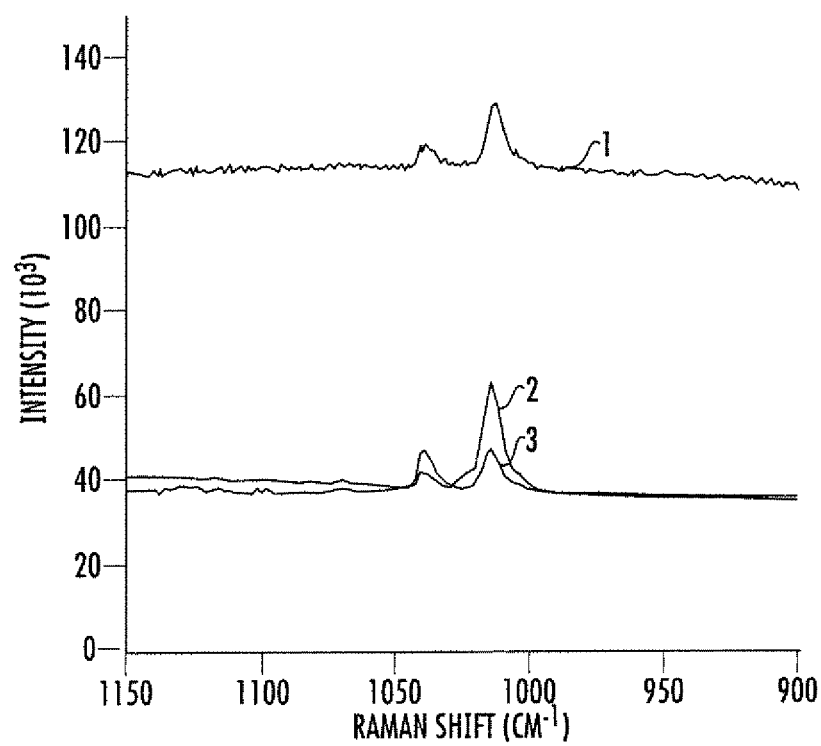
FIG. 10A shows the Raman signal of a 0.2 weight % pyridine solution in water on various SERS substrates
Figure 10B:
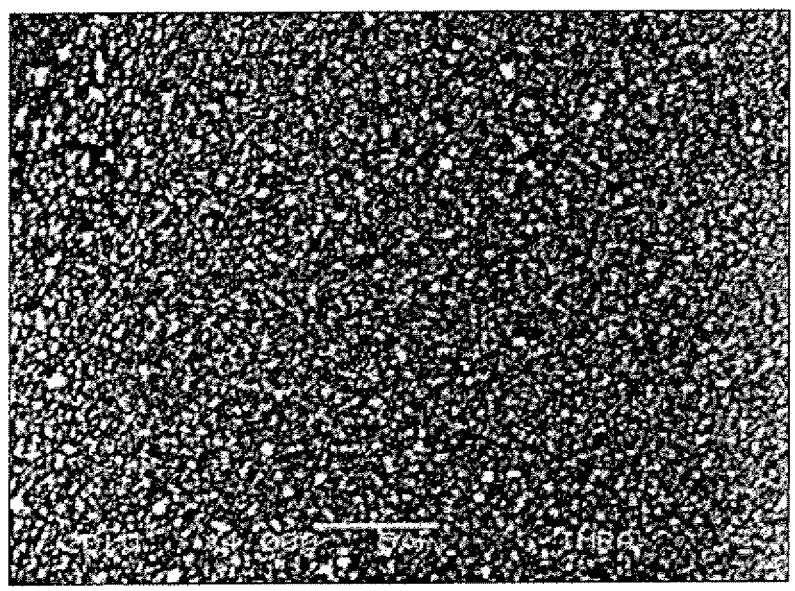
FIG. 10B is a SEM image of an Au thin film made by backside transferred PLD onto a substrate in accordance with the present invention.

In a next experiment Klarite™ was compared to substrates prepared according to the present invention by backside transferred PLD of Au, shown in FIG. 4, or by DC magneto sputtering of Au. FIG. 10A shows the Raman signal of a 0.2 weight % solution of pyridine in water using a Klarite™ substrate, line 1, a backside transferred PLD, line 2, and a DC magneto sputtering, line 3. The DC magneto sputtering produced a thickness of the Au of 2.5 nanometers. SERS enhancement was observed for all three substrates. The SERS enhancement of spectrum line 3 is not as good as Klarite™, but the fluorescent background was reduced. The backside transferred PLD film also showed excellent SERS enhancement, line 2. The line width, line density and size distribution of the metal particles can be engineered to optimize Raman enhancement using backside transferred PLD. In case of backside transferred PLD, surface coverage of the metal layer, as shown in FIG. 10B, can be more than 100% to show SERS enhancement. FIG. 10B is a SEM image of the Au SERS film made by backside transferred PLD. It is worth mentioning that the backside transferred PLD Au films have a red color, which corresponds with the Au plasmonic frequency having an absorption peak of about 520 nanometers.

Backside transferred PLD is utilized for making SERS substrates herein. Similar printing techniques using pulsed laser deposition will be utilized for the SERS substrates also. The configuration described in FIG. 4 can be modified for other printings. The target 40 can be replaced by a metal foil for the printing of metal coatings. This can also be interpreted as a backside transfer pulsed laser deposition. Or a laser beam can be irradiated through a target 40 to coat the metal onto a substrate 44, referred to here as forward transfer pulsed laser deposition. In that case the substrate 44 is either transparent or non-transparent to the laser beam, either will work.

Figure 11:
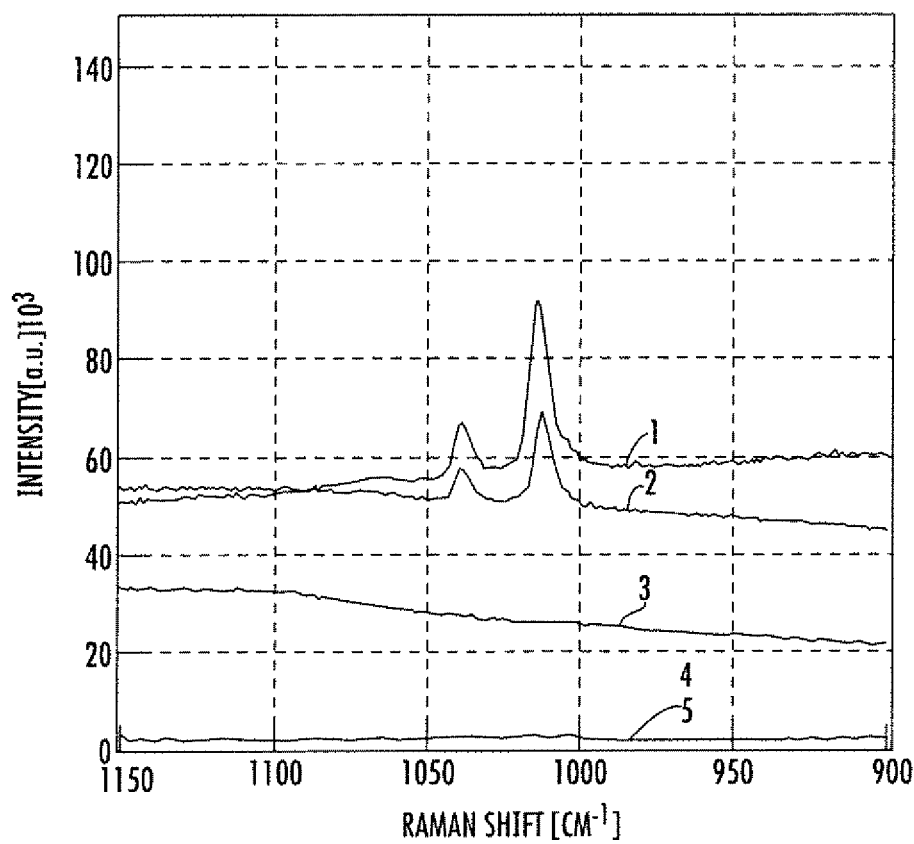
FIG. 11 shows the Raman signal of a 0.2 weight % pyridine solution in water from substrates according to the present invention wherein the substrates have been pre-coated prior to deposition of the SERS active metal coating.

In a next series of experiments the effect of a pre-coating surface on the SERS enhancement was investigated. Glass substrates were initially coated with either Au or Pt using a sputter coater to an expected thickness of 100 nanometers. The sputter conditions were as follows: 40 mA, 0.8 mbar, and 300 sec. Then SERS active metal Au thin films are grown onto these pre-coated substrates using PLD per the present invention. The PLD laser conditions for the Au thin films were laser power of 6.5 W, 1 MHz burst repetition rate, and 2 pulses per burst. The deposition rate was about 0.03 nanometers/second and the Au films were coated to a thickness of 3 nanometers. The Raman signal of a 0.2 weight % solution of pyridine in water was then determined for the substrates and the results are shown in FIG. 11. The spectra are as follows: line 1 is an Au film onto an Au pre-coating; line 2 is an Au film onto bare glass; line 3 is the bare glass with no Au film; line 4 is the Pt pre-coating with no Au coating; and line 5 is an Au film grown on a Pt pre-coating. As expected there is no SERS enhancement on bare glass, line 3. Lines 1 and 2 show that there is SERS enhancement observed for Au films deposited onto either a pre-coating of Au or onto bare glass. The signal enhancement seems best for a pre-coating of Au on the glass and shows the importance of a rougher surface for SERS enhancement. The Pt pre-coating alone or after an Au coating according to the present invention, lines 4 and 5 respectively, show only weak SERS enhancement. These results demonstrate that by changing the coating materials beneath the SERS active metals, the SERS enhancement can be engineered.

As for a coating under the Raman active metals there are numerous materials that can be considered: metals such as Cr, Co, Ni, Cu, Pd, Ag, Pt, and Au; metal oxide such as 3d transition metal oxides including Ti, V, Cr, Mn, Fe, Co, Ni, Cu, and Zn.

Figure 12A:
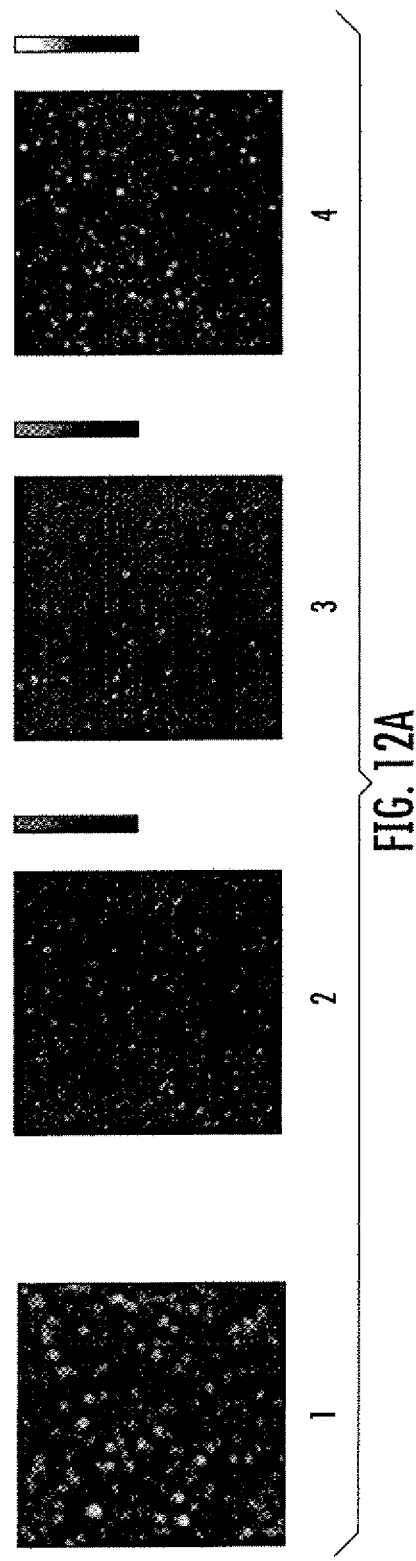
FIG. 12A shows Atomic Force Microscope images of Ag thickness gradient thin films on a sapphire substrate and FIG. 12B shows a TEM image of Ag nanoparticles prepared according to the present invention.
Figure 12B:
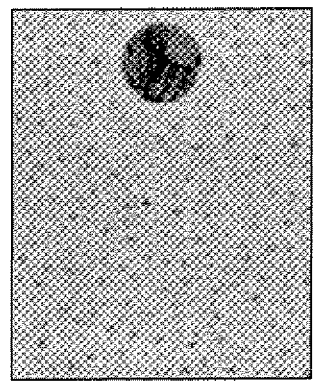

FIG. 12A shows AFM images of Ag thickness gradient thin films on a sapphire substrate. The thickness gradient region A described in FIG. 3A is 7 millimeters long. The designed thickness varies from 0 nanometers to 14 nanometers. The laser power, the burst frequency, and the number of the burst pulses for growth of the Ag thin films used were 73 W, 1 MHz, and 2 pulses, respectively. The deposition rate is about 0.06 nanometers per second. The designated thicknesses in images 1-4 are 2, 6, 10, and 14 nanometers, respectively. FIG. 12B illustrates a transmission electron microscope (TEM) image of Ag nanoparticles fabricated onto a carbon coated TEM grid. The designed thickness is 1 nanometers. From the results, we can also identify at least two groups of different sized nanoparticles, similar to what was seen for the Au films above. A first group has a particle size of about 2 to 10 nanometers in diameter and a second group has a particle size of about 10 to 100 nanometers in diameter. The ratio and/or amount of these different size groups of particles can be adjusted by changing the designed thickness or growth conditions of the Ag thin film. It also appears that the population of the second group of particles in this Ag film is less than what was seen above in Au thin film. The result may originate from the difference in ablation threshold between Au and Ag.

Figure 13:
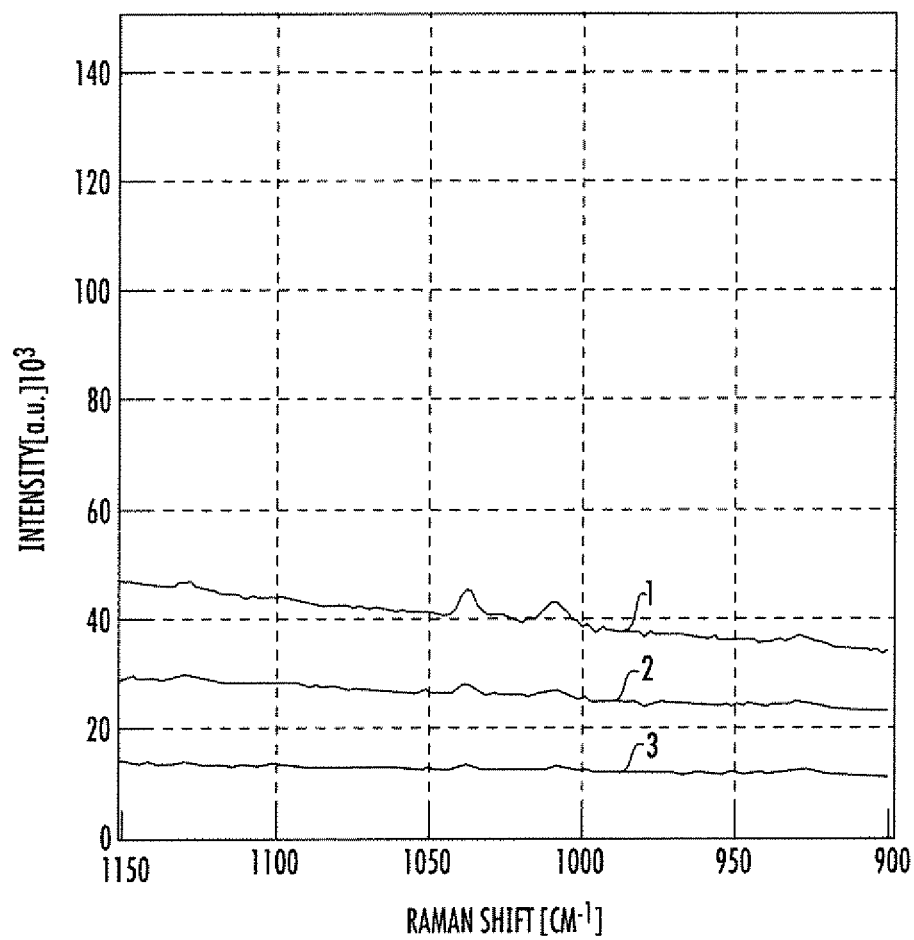
FIG. 13 shows Raman signals of a 0.2 weight % pyridine solution in water from Ag SERS active metal substrates prepared according to the present invention.

In another series of experiments, the present invention was used to create a gradient of the SERS active metal Ag onto a glass substrate. The length of the gradient was 20 millimeters and the thickness of the Ag was varied from 0 to 10 nanometers. The laser conditions for growth of the gradient were as follows: laser power of 1W, burst frequency of 100 kHz, and 8 pulses per burst. FIG. 13 shows Raman signals of a 0.2 weight % solution of pyridine in water using the substrate. The spectra lines are as follows: line 1 is 10 nanometers of Ag; line 2 is 5 nanometers of Ag; and line 3 is 1 nanometers of Ag. The greatest SERS enhancement was observed with the 10 nm thick Ag coated substrate, line 1. The results demonstrate that for Ag, similar as shown for Au in FIG. 7, the present invention can be used to easily optimize the SERS enhancement of Ag on substrates. Clearly the best thickness of a given SERS active metal on a substrate is determined by the identity of the active metal and may be influenced by a pre-coating or the molecule to be identified.

In some embodiments above a substrate for SERS is discussed. Surface enhanced resonance Raman spectroscopy (SERRS), surface enhanced hyper-Raman spectroscopy (SE-HRS), surface enhanced coherent anti-Stokes Raman spectroscopy (SECARS), or surface enhanced infrared absorption (SEIRA) are also expected to show similar enhancement from similar nanoparticle thin film structures prepared as disclosed herein. The importance of a mixture of different sized groups in the thin film can be interrupted to mean that the Plasmon frequency can be precisely tuned by modifying the ratio or the amount of these different groups of particles in the thin film. Thus, in one embodiment it is preferable to have one group of particles in the size range of 0.5 to 10 nanometers and another group having a size range of 10 to 1000 nanometers.

The randomness of the nanoparticles may also play an important role for signal stability and other facts of superiority of this invention for enhanced Raman spectroscopy. This random structure will work very efficiently to get stable and repeatable Raman enhancement for the image area is large enough such as more than 2 micrometers in scale. Because the nanoparticles are small enough compared with the imaging or detection area, the surface can be assumed to be uniform.

In summary, the inventors have disclosed a method and apparatus to prepare a substrate for surface enhanced Raman spectroscopy (SERS) using physical vapor deposition methods, in particular, pulsed laser deposition using ultrafast pulsed lasers, backside transfer PLD, and sputtering deposition. The methods provided are fast, inexpensive and very reproducible. In addition, the disclosed methods provide significantly more enhancement than is observed with the commercially available product Klarite™. The method can be adapted to use a wide variety of SERS active metals and is easily tunable for different conditions, substrates and compounds to be analyzed. The method can be further adapted to use in a wide variety of spectroscopy including surface enhanced infrared absorption (SEIRA) using plasmon coupling for enhancements of chemical or biological specificity and sensitivity. The current methods also use far less active metal to achieve the enhancement compared to previous solutions. The single step process of the present invention also greatly reduces production time for SERS substrates compared to prior systems. The SERS substrates and process disclosed according to the present invention can also be used for surface enhanced resonance Raman spectroscopy (SERRS), surface enhanced hyper-Raman spectroscopy (SE-HRS), or surface enhanced coherent anti-Stokes Raman spectroscopy (SECARS). The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A device for enhancement of Raman spectroscopy comprising:
   a plurality of nanoparticles, said nanoparticles having a multimodal size distribution with at least a first population having a diameter of from 2 to 10 nanometers and at least a second population having a diameter of from 25 to 50 nanometers, said nanoparticles being free from any surfactants; and
   a substrate having said plurality of nanoparticles coated onto a surface of said substrate to form a coated surface, and wherein the thickness of said coated surface formed from said plurality of nanoparticles on said substrate increases in a predetermined manner from an initial thickness of more than 0 nanometers to a final thickness of 200 nanometers or less along a portion of said substrate to produce a thickness gradient of said coated surface on said substrate, and wherein said coated surface provides plasmon coupling for enhancements of chemical or biological specificity and sensitivity of said substrate to a material placed on said coated surface and wherein said nanoparticles being free from surfactants permits detectability of the Raman-inactive vibration modes up into the infrared spectral range.

2. The device of claim 1, wherein said coated surface provides plasmon coupling for enhancements of Raman spectroscopy of said device to materials placed on said coated surface.

3. The device of claim 1, wherein said initial thickness is more than 0 nanometers and the final thickness is less than or equal to 100 nanometers.

4. The device of claim 1, wherein said nanoparticles comprise Au, Ag, Cu, Pt, alloys thereof, composites thereof, or mixtures thereof.

5. The device of claim 1, wherein said substrate surface has a surface roughness of less than 3 microns.

6. The device of claim 1, wherein said substrate comprises a glass, a semiconductor, a dielectric, an organic film, or a metal foil.

7. The device of claim 1, wherein said surface of said substrate has been pre-coated with at least one material prior to coating said plurality of nanoparticles onto said surface.

8. The device of claim 7, wherein said pre-coated material comprises a metal, a dielectric or a mixture thereof.

9. The device of claim 1, wherein the substrate has enhanced Raman spectroscopy comprising surface enhanced Raman spectroscopy (SERS), surface enhanced resonance Raman spectroscopy (SERRS), surface enhanced hyper-Raman spectroscopy (SEHRS), or surface enhanced coherent anti-Stokes Raman spectroscopy (SECARS).

10. The device of claim 1, wherein the substrate has surfaced enhanced infrared absorption (SEIRA).

11. A method of forming a device for use in a performing plasmon coupling for enhancements of the electric fields and enhancements of Raman spectroscopy and enhancements of the chemical or biological specificity and sensitivity of the substrate for Raman spectroscopy comprising:
   simultaneously creating and applying a plurality of nanoparticles having a multimodal size distribution with at least a first population having a diameter of from 2 to 10 nanometers and at least a second population having a diameter of from 25 to 50 nanometers of a Raman active material from a bulk source material onto a surface of a substrate in a single step by a process comprising one of pulsed laser deposition, backside transfer pulsed laser deposition, forward transfer pulsed laser deposition, wherein said creating and applying said plurality of nanoparticles comprises using laser pulses having a pulse duration in the range from about 10 femtoseconds to 200 picoseconds, thereby forming a Raman active substrate on said surface of said substrate in a single step.

12. The method of claim 11, wherein the pulsed laser deposition is carried out at a pressure of from an ultrahigh vacuum of $<1\times10^{-10}$ mbar to 1 atmosphere.

13. The method of claim 11, comprising using a pulsed laser having a wavelength ranging from 200 nanometers to 2000 nanometers.

14. The method of claim 11, comprising using a pulsed laser having a repetition rate less than about 500 MHz.

15. The method of claim 11, comprising using a pulsed laser having a repetition rate ranging from 1 kHz to 5 MHz.

16. The method of claim 11, comprising forming a Raman active surface for surface enhanced Raman spectroscopy (SERS), surface enhanced resonance Raman spectroscopy (SERRS), surface enhanced hyper-Raman spectroscopy (SEHRS) or surface enhanced coherent anti-Stokes Raman spectroscopy (SECARS).

17. The method of claim 11, comprising forming an active surface for surface enhanced infrared absorption.

18. A product made by the method of claim 11, said product comprising a substrate having a layer of nanoparticles coated thereon, wherein said layer of nanoparticles provides plasmon coupling for enhancements of chemical or biological specificity and sensitivity to materials placed on a surface of the substrate.

19. The product of claim 18, wherein said layer of nanoparticles provides for plasmon coupling for enhancements of Raman spectroscopy to materials placed on a surface of the substrate.

20. The product of claim 18, wherein at least a portion of said layer of nanoparticles is in direct contact with said substrate surface.

21. The product of claim 18, wherein a thin film is disposed between said substrate surface and at least a portion of said layer of nanoparticles.

22. The method of claim 11 comprising using a movement of a mask during said single step process to create a thickness gradient of increasing thickness of applied nanoparticles on said surface of said substrate wherein an initial thickness of said nanoparticles is more than 0 nanometers thick and wherein a final thickness of said nanoparticles is 200 nanometers or less.

23. A method of forming a device for use in a performing plasmon coupling for enhancements of the electric fields and enhancements of Raman spectroscopy and enhancements of the chemical or biological specificity and sensitivity of the substrate for Raman spectroscopy comprising:
   simultaneously creating and applying a plurality of nanoparticles of a Raman active material from a bulk source material onto a surface of a substrate in a single step by a process comprising one of pulsed laser deposition, backside transfer pulsed laser deposition, forward transfer pulsed laser deposition, or sputtering, said plurality of nanoparticles having a multimodal size distribution with at least a first population having a diameter of from 2 to 10 nanometers and at least a second population having a diameter of from 25 to 50 nanometers and said process further comprising using a movement of a mask during said single step process to create a thickness gradient of increasing thickness of applied nanoparticles on said surface of said substrate wherein an initial thickness of said nanoparticles is more than 0 nanometers thick and wherein a final thickness of said nanoparticles is greater than said initial thickness and is 200 nanometers or less, thereby forming a Raman active substrate on said surface of said substrate in a single step said Raman active substrate having a thickness gradient on said surface.

24. The method as recited in claim 11 further comprising creating and applying said nanoparticles in the absence of any surfactants.

25. The method as recited in claim 23 further comprising creating and applying said nanoparticles in the absence of any surfactants.

* * * * *

UNITED STATES PATENT AND TRADEMARK OFFICE
CERTIFICATE OF CORRECTION

PATENT NO. : 8,836,941 B2
APPLICATION NO. : 12/951524
DATED : September 16, 2014
INVENTOR(S) : Makoto Murakami et al.

It is certified that error appears in the above-identified patent and that said Letters Patent is hereby corrected as shown below:

In the Specification,

Column 2, Line 15 "Ace. Chem." should be --Acc. Chem.--.
Column 11, Line 47 "73" should be --7.3--.

Signed and Sealed this
Nineteenth Day of May, 2015

Michelle K. Lee
*Director of the United States Patent and Trademark Office*